US009488626B2

(12) United States Patent
Suedel et al.

(10) Patent No.: US 9,488,626 B2
(45) Date of Patent: Nov. 8, 2016

(54) DIAGNOSTIC METHOD FOR POPPET VALVES AND MEASURING DEVICE FOR CARRYING OUT SAID METHOD

(75) Inventors: Matthias Suedel, Ratekau (DE); Peter Fahrenbach, Hamburg (DE); Bernd Porath, Breitenfelde (DE)

(73) Assignee: GEA TUCHENHAGEN GMBH, Büchen (DE)

( * ) Notice: Subject to any disclaimer, the term of this patent is extended or adjusted under 35 U.S.C. 154(b) by 766 days.

(21) Appl. No.: 13/821,651

(22) PCT Filed: Sep. 6, 2011

(86) PCT No.: PCT/EP2011/004488
§ 371 (c)(1),
(2), (4) Date: May 23, 2013

(87) PCT Pub. No.: WO2012/031743
PCT Pub. Date: Mar. 15, 2012

(65) Prior Publication Data
US 2013/0228005 A1    Sep. 5, 2013

(30) Foreign Application Priority Data
Sep. 9, 2010  (DE) .................. 10 2010 044 891

(51) Int. Cl.
*G01N 33/00* (2006.01)
*F16K 1/44* (2006.01)
(Continued)

(52) U.S. Cl.
CPC .............. *G01N 33/00* (2013.01); *F16K 1/446* (2013.01); *F16K 37/0083* (2013.01); *G01B 5/30* (2013.01); *G01B 7/18* (2013.01)

(58) Field of Classification Search
CPC ..... F16K 1/446; F16K 37/0083; G01B 5/30; G01B 7/18; G01N 33/00
USPC ............ 73/47.48, 114.79, 862.381, 862.451, 73/862.392, 862.582, 276, 863.86, 865.9
See application file for complete search history.

(56) References Cited

U.S. PATENT DOCUMENTS 4,428,223 A * 1/1984 Trevisan ............. F16K 37/0083
73/1.72
4,882,937 A * 11/1989 Leon ....................... G01B 7/16
73/168

(Continued)

FOREIGN PATENT DOCUMENTS

DE        19608792       9/1997
DE        29811115       10/1999

(Continued)

*Primary Examiner* — Hezron E Williams
*Assistant Examiner* — Marrit Eyassu
(74) *Attorney, Agent, or Firm* — Vidas Arrett & Steinkraus

(57) ABSTRACT

The invention relates to diagnostic methods according to the preamble of the equivalent claims 1 and 2, with which the state of a poppet valve in the course of the switching cycles and/or events thereof, such as the occurrence of pressure shocks or surges during continuous operation is/are monitored continuously, the measured signals are stored and the stored measured signals are interpreted in a targeted manner and early indication of cases of damage is carried out. According to a preferred variant of the diagnostic method, said aim is achieved in that at the same time as the force-time curve of the actuating force or the reaction force (F1($t$); F2($t$)), a displacement-time curve (h($t$)) of the displacement (h) of the at least one closing element (8*) is measured, in that the force-time curve of the actuating force or of the reaction force (F1($t$); F2($t$)) and the displacement-time curve (h($t$)) are combined with each other and used to determine a force-displacement curve of the actuating force or the reaction force (F1($h$); F2($h$)), in that the current force-displacement curve of the actuating force (F1($h$)) or the reaction force (F2($h$)) of a switching cycle, in each case determined over the operating period or lifetime of the poppet valve (100), is compared with an earlier, stored curve, in that deviations are determined from the comparison, in that, within a predefined tolerance range for said deviations, the latter are accepted, and in that, when said deviations exceed the predefined tolerance range, a message and/or a control signal is/are generated.

14 Claims, 11 Drawing Sheets

(51) Int. Cl.
  *G01B 5/30* (2006.01)
  *G01B 7/16* (2006.01)
  *F16K 37/00* (2006.01)

(56) References Cited

U.S. PATENT DOCUMENTS

| | | |
|---|---|---|
| 6,382,226 B1 | 5/2002 | Larson et al. |
| 7,032,878 B2 * | 4/2006 | Coura ............... F16K 31/003 251/129.04 |
| 2009/0024258 A1 * | 1/2009 | Varga ............... F16K 37/0083 700/301 |

FOREIGN PATENT DOCUMENTS

| | | |
|---|---|---|
| EP | 0174384 | 3/1986 |
| EP | 1387975 | 2/2004 |
| EP | 1529176 | 5/2005 |
| JP | 04-185983 | 7/1992 |
| JP | 2006-184193 | 7/2006 |
| WO | 96/30684 | 10/1996 |
| WO | 99/60369 | 11/1999 |
| WO | 02/093058 | 11/2002 |

* cited by examiner

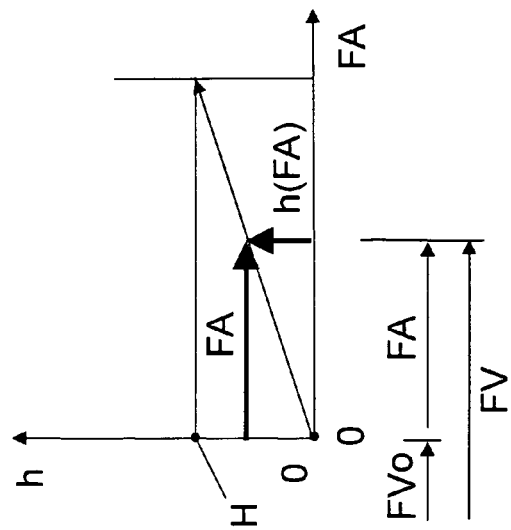
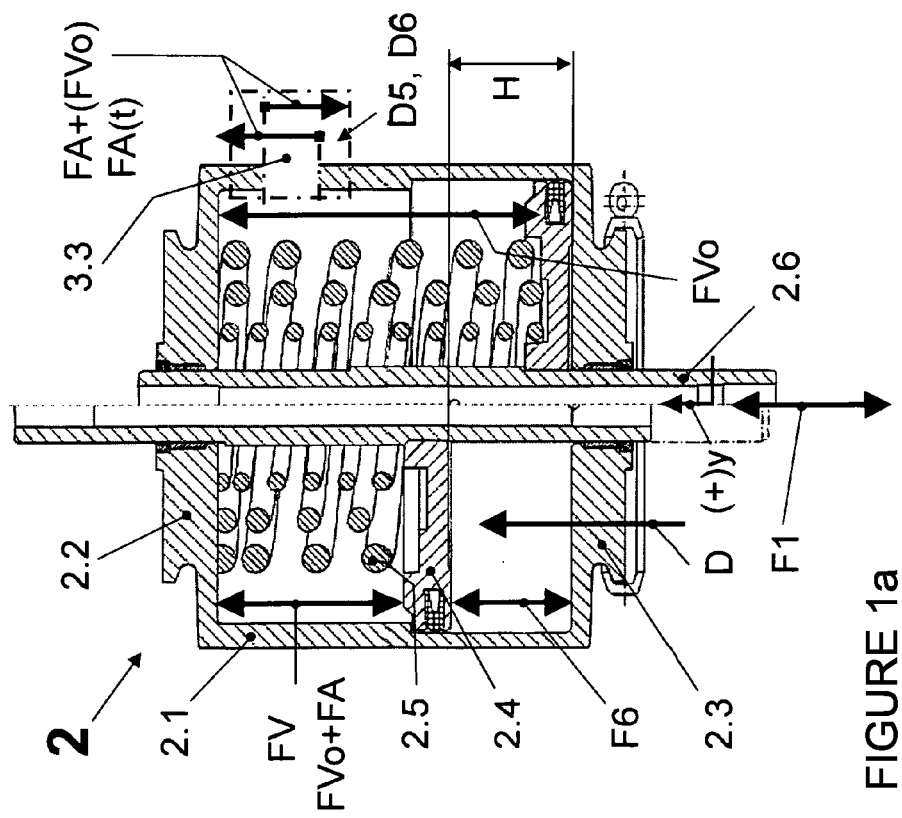
FIGURE 1b
FIGURE 1a

DIAGNOSTIC METHOD FOR POPPET VALVES AND MEASURING DEVICE FOR CARRYING OUT SAID METHOD

CROSS-REFERENCE TO RELATED APPLICATIONS

This application is a U.S. National Stage Application which claims priority to PCT/EP2011/004488 filed Sep. 6, 2011, which claims priority to DE 10 2010 044 891.5 filed Sep. 9, 2010.

STATEMENT REGARDING FEDERALLY SPONSORED RESEARCH

Not applicable

BACKGROUND OF THE INVENTION

The invention relates to a diagnostic method for poppet valves with which an actuating force representing an action force that is generated by a drive of the poppet valve is measured for at least one closing element of the poppet valve in the form of a force-time curve, the actuating force is either measured directly or from the reaction force resulting from the actuating force in the poppet valve, wherein the actuating force or the reaction force is determined by measuring the expanding deformations caused therefrom, and the measured, current force-time curve of the actuating force or of the reaction force is saved and subjected to an evaluation. The poppet valves are in particular shutoff valves, double seal valves, double seat valves, or seat-cleaning double seat valves. A spring-piston drive preferably functions as the drive for these valves that is supplied with pressurizing medium, preferably compressed air. Such drives work in that a spring closes or a spring opens the closing element and its seat surface (shutoff valve, double seal valve), or both closing elements and their respectively assigned seat surface (double seat valve). Drives with a dual-acting piston which is supplied with pressurizing medium on both sides are also included.

In the case of a shutoff valve that is designed as a poppet valve with a single closing element (hereinafter, this embodiment will be restricted to the designation of "shutoff valve"), a seat seal arranged on the closing element acts on the assigned seat surface in the direction of the displacement. The latter can be oriented perpendicular to the direction of the displacement. In this case, the expression "axially acting seat seal" is used (seal in pressure engagement). However, the seat surface can be conically designed so that the reaction force exerted by the seat surface on the seat seal generates an axially and radially acting sealing force (seal in pressure and sliding engagement). The closing element can, however, also be designed as a valve piston with a seat seal that is arranged on the lateral surface of the valve piston and glides along a cylindrical seat surface under radial pretension (seal in sliding engagement).

The above seal configurations are equally transferable to double seal valves (and seat cleaning) double seat valves. In contrast to the aforementioned shutoff valve, another shutoff valve to be understood as a double seal valve has a single closing element with two seat seals at an axial distance from each other, i.e., in the direction of displacement, that enclose a leakage cavity between themselves and in conjunction with assigned seat surfaces and the closing element, the leakage cavity being connected via at least one connecting path to the surrounding area of the double seal valve.

A (seat-cleaning) double seat valve possesses two independently actuatable closing elements that enclose a leakage cavity between themselves which is connected via at least one connecting path to the surrounding area of the double seat valve. Each closing element possesses one assigned seat surface. During the opening movement, first the independently driven closing element opens that, as its opening movement continues, comes into contact with the other closing element which it simultaneously transfers into the open position. The aforementioned sequence of steps accordingly reverses during the closing process. Double seat valves differ from those that are seat-cleaning only in that the assigned drive is able to transfer the two closing elements into partially open positions that are separately controllable.

The closing element is connected to the drive piston of the drive briefly outlined above by means of an assigned adjusting rod. In the case of the double seat valve, only the independently-driven closing element has a fixed connection to the drive piston in the drive, whereas the dependently-driven closing element is arranged in a relatively movable manner with reference to the independently driven closing element and abuts it under initial spring tension. In regard to the closing element and seal configuration, double seat valves are preferably used today with two closing elements that function as a seat disc (double seat valve of the first kind), or with one closing element formed as a seat disc and one formed as a valve piston, wherein the valve piston represents the independently driven closing element (double seat valve of the second kind).

BACKGROUND OF THE INVENTION

The status of a poppet valve in regard to:
Its friction behavior in the housing leadthroughs for its adjusting rod(s),
Its pressure and flow forces impinging on the enclosing element or closing elements,
The status of its seat seal(s),
Its drive (integrity of the springs and drive piston, among other things), and
Its other status parameters
are reflected in particular in the engagement of the actuation force (action force) of the adjusting rod(s).

The pressure and flow forces consisting of static pressure (overpressure, underpressure) and/or dynamic pressure (inflow) comprise the planned forces that result during the regular operation of a processing system in which the poppet valve is arranged; however, they also comprise unplanned forces such as pressure surges or shocks in the valve housing supplied with the respective fluid. These unplanned forces can exceed the planned ones many times over, they affect the relevant closing element and hence the adjusting rod that is fixedly connected thereto, and they also influence the interaction between and equilibrium of forces in the drive unless they are largely compensated by so-called pressure balanced pistons, or experience corresponding opposing forces from the seat surface of the closing element.

A measuring system is described in DE 298 11 115 U1 for measuring the spindle force in fittings in which, among other things,
a force sensor is arranged in a frictional connection at a position in the direction of force of the acting spindle force,
The force sensor can be a strain gauge,
The force sensor is, for example, mounted on the spindle or on a connecting screw in the flange between the fitting and drive.
In addition to the strain gauge functioning as the force sensor, the known measuring system has a calibration measuring device with which the force sensor is calibrated. The calibration measuring device is removed while the system is operating. The object of the described measuring system is to provide a measuring system that is optimally suitable for the measuring procedure in WO 96/30684 A1 in which the spindle force is measured in situ and evaluated using procedures for analyzing the time signal, and furthermore enables the spindle force to be continually measured.

A specific solution of how to measure the spindle force of a valve driven by a spindle/nut system is only disclosed in conjunction with a calibration measuring device. Beyond that, only a force sensor is described that can be mounted to a connecting screw on a flange between the fitting and drive. Whether such an arrangement is suitable to, for example, reliably detect a defect in the seat seal, a worn or corroding rod leadthrough, an incomplete closing, opening or partially open position (seat cleaning), or a pressure surge is not disclosed, discussed or suggested.

A diagnostic method is known from U.S. Pat. No. 4,882,937 A which is based on a force-movement curve. The movement of the valve rod in a sensor which basically consists of a coil with a plurality windings, induces stress which is proportional to the speed of the axial movement of the valve piston. A speed-time curve is accordingly determined that is combined with the speed-time curve which is also measured. The actuating force of the valve rod is not directly measured; instead, a suitable sensor measures its reaction force which arises in a connecting housing between a valve housing and a drive which causes the actuating movement of the valve piston.

Specific solutions for achieving a practical diagnostic method for poppet valves having a spring piston drive supplied with pressurizing medium and a measuring device for performing it are consequently not disclosed in the aforementioned prior art. The aforementioned prior art also does not disclose any indications and suggestions of how to glean such information from the obtained measuring signals.

Based on the state-of-the-art, the object of the present invention is to provide a diagnostic method for poppet valves of the generic type with which the status of a poppet valve e.g. regarding its friction behavior in the leadthroughs for its adjusting rod(s),
the status of its seat seal(s),
mechanical damage to its interacting components (such as springs in the drive; spring failure)
the displacement position of its closing element/closing elements during its switching cycles and/or
events such as the occurrence of pressure surges or shocks in ongoing operation, are continously monitored, the measuring signals are saved and the saved measuring signals are usefully interpreted, and early notification of damage is provided. It is furthermore the object of the invention to present a measuring device to perform the diagnostic procedure with which the aforementioned states and events can be reliably and reproducibly detected.

TECHNOLOGICAL BACKGROUND

Before the invention is explained further, first the basic force relationships will be described below when a shutoff valve and double seat valve are switched that make it possible to detect the force-time curve or the force-displacement curve relevant for the state of a poppet valve in the form of the actuating force functioning as an action force, or in the form of a reaction force generated by the actuating force in the poppet valve. The force relationships in the process of closing a poppet valve 100 are described by way of example in a spring-closing shutoff valve 110 (FIG. 1) and in a spring-closing double seat valve 120 (FIG. 2).

Shutoff Valve (FIG. 1)

FIG. 1 in the drawing illustrates the interaction of forces during a switching cycle of a shutoff valve 110, wherein the closing process up to the closed position SS (displacement movement in the (−)y direction) in this switching cycle will be considered. In the closed position SS, a seat seal 16* acts with a sealing force F5 in the (+)y direction on a single closing element 8* and hence on an adjusting rod 8a*. During the closing process selected as an example, the frictional forces F3 continue to act in the leadthrough of the adjusting rod 8a* through a second valve housing part 1b of a valve housing 1, namely in the guide ring (top ring which is not shown) and in the rod seal (bottom ring which is not shown) in the (+)y direction. Moreover, if applicable, flow forces and/or pressure forces F4 act in the second and first valve housing part 1b, 1a on the closing element 8* in the (+)y or (−)y direction (static pressure, including suction in the case of underpressure, dynamic pressure, overall pressure, pressure surge). The following results for an actuating force F1 acting on the adjusting rod 8a* from the force equilibrium in the adjusting rod 8a* below the top end of a lantern housing 4 (positive upward direction of force +y):

$$-F1+F3+/-F4+F5=0 \qquad (1)$$

$$F1=F3+/-F4+F5. \qquad (1a)$$

The actuating force F1 of the valve rod 8a* (action force; equation (1a)) is generally a compressive force during the closing process (rod friction F3 acting in the (+)y direction) relative to the adjusting rod 8a*. In this result, the influence of the flow force F4 is not considered.

During the opening process, the respective directions of force correspondingly reverse up to and including the sealing force F5 which acts on the closing element 8* and continues to act in the (+)y direction as long as the seat seal 16* is pressed against an assigned seat surface 12*. In this result, the influence of the flow force F4 is not considered either.

The actuating force F1 as an action force between a drive 2 and the valve housing 1, in particular in the interaction between the closing element 8* and the seat surface 12* when the closing element 8* enters or exits the seat surface 12*, experiences its opposing force, a reaction force F2, in the lantern housing 4 in a particularly clear manner that establishes a fixed connection between valve housing 1 and the drive 2, wherein the lantern housing 4 in a preferred embodiment consists of two connecting bars, two lantern crossmembers 4a, 4b, that are arranged diametrically opposite from each other. Each change in the action force F1 below the drive 2, that is, below the top end of the lantern housing 4, experiences its respective opposing reaction force F2 in the lantern housing 4. The following holds true for the equilibrium of forces (equations (2), (2a)) in the valve housing 1 held by the lantern housing 4 ((+)y direction):

$$-F+F2=0 \qquad (2)$$

$$F1=F2 \qquad (2a)$$

The forces acting on the adjusting rod 8a* within the drive do not generate any opposing forces in the lantern housing 4; they are fully compensated in the drive 2. During the closing process, pressure forces act on the adjusting rod 8*, and tensile forces act on the lantern housing 4. During the opening process, the directions of stress correspondingly reverse once the sealing pressure no longer exists and the closing element 8\* does not experience the flow force F4 overcoming the frictional force F3 in the (+)y direction. The following also applies:

In the closed position SS of the shutoff valve 110, the closing element 8\* abuts the seat seal 16\* and hence the seat surface 12\* with a minimum pretension FVo of a spring 2.5 provided in the drive 2 (FIG. 1*a*, 1*b*). This action and actuating force F1 is expressed as compressive force in the adjusting rod 8*a*\*. In the lantern housing 4, it generates the reaction force F2 in the form of an equally large tensile force (to establish the equilibrium of forces in the shutoff valve 110 below the drive 2).

If the shutoff valve 110 is opened, then these forces in the seat region decrease over the relatively short path to relax the seat seal 16\*. Once force is no longer exerted on the closing element 8\* after the seat surface 12\* has been left—this simplification is only provided at this juncture to illustrate consequences—the lantern housing 4 is free from tractive or pressure forces. The necessary equilibrium of forces of the controlled drive 2 under pretension FV from the spring 2.5 (FIG. 1*a*, 1*b*), which is greater than the original minimum pretension FVo in the closed position SS, is generated within the drive 2.

If additional frictional forces F3 act on the adjusting rod 8*a*\*, such as at the leadthrough for the adjusting rod 8*a*\* through the valve housing 1, or additional flow forces F4 act on the closing element 8\* and hence in turn on the adjusting rod 8*a*\*, then these forces necessarily attenuate as reaction forces F2 in the lantern housing 4.

The most significant exertion of force on the lantern housing 4 occurs when the closing element 8\* and its seat seal 16\* enter and exit the seat surface 12\*, wherein at most, the minimum pretension FVo of the spring 2.5 is generated in the closed position SS of the shutoff valve 110 in the lantern housing 4. Other aforementioned forces can overlap this interplay of forces.

Double Seat Valve (FIG. 2)

The same considerations regarding the interplay and equilibrium of forces in the above-explained shutoff valve 110 apply to a poppet valve 100 designed as a double seat valve 120, 130 according to FIG. 2 with the closing element and seat configuration and resulting movement kinematics known from EP 1 529 176 B1 (double seat valve of the first type), or a double seat valve of the second type with an independently driven first closing element designed as a valve piston, and a second dependently-driven closing element designed as a seat disc (DE 196 08 792 C2). However, the actuation force and reaction force curves of the two double seat valve types significantly differ when the closing elements enter and exit the assigned seat surfaces. These differences will be further explained with reference to the related measuring results below.

The double seat valve 120, 130 (FIG. 2) has a first closing element 6 independently driven by a spring-closing drive 2 and a second closing element 8 driven dependently by the latter which enclose a leakage cavity 7 between themselves, wherein a second adjusting rod 8*a* that, for example, is designed as a hollow rod and is securely connected to the second closing element 8 abuts a first adjusting rod 6*a* that is under the pretension of a second spring 2.7 and is concentrically guided through the hollow rod 8*a* and is securely connected to the first connecting element 6. Whereas a first seat seal 14 of the first closing element 6 in its closed position is pressed by the spring 2.5 in the drive 2 against an assigned first seat surface 10, a second seat seal 16 of the second closing element 8 is correspondingly pressed by the second spring 2.7 against an assigned second seat surface 12.

The above description of the interplay of forces in a shutoff valve 110 can be transferred without restriction to any closing element 6, 8 since comparable initial forces can be exerted on each of them (F3.1, F3.2; F4.1, F4.2; F5.1, F5.2). Arranged between the two closing elements 6, 8 is a middle seal 18 that engages with the second closing element 8 during the opening movement of the first closing elements 6 proceeding from the closed position SS according to FIG. 2 after a partial displacement of the first closing element 6, and it remains engaged in a subsequent joint open (OS) or partially open position, but remains disengaged in the closed position SS shown in FIG. 2. The two closing elements 6, 8 are accordingly coupled and decoupled over the course of a switching cycle consisting of an opening and closing movement under the conditions of deformation of the middle seal 18.

As shown in FIG. 2, a balance of forces and equilibrium of forces can be described for each closing element 6, 8 corresponding to equation (1a) with the following results (equations (3), (4)):

$$\text{first closing element 6: } F1.1 = F3.1 +/- F4.1 + F5.1. \tag{3}$$

$$\text{second closing element 8: } F1.2 = F3.2 +/- F4.2 + F5.2. \tag{4}$$

Consequently the following holds true for the equilibrium of forces in a piston rod 2.6 below the lantern housing 4 where a first actuating force F1.1 and a second actuating force F1.2 are combined to form actuating force F1:

$$F1 = F1.1 + F1.2 \tag{5}$$

The following holds true for the reaction force F2 in the lantern housing 4 with equation (2a):

$$F1 = F2 = F1.1 + F1.2. \tag{6}$$

Due to the fact that the seat surface 14, 16 of each control element 6, 8 enters and exits the assigned seat surface 10, 12 independent of the other, the result of equation (6) shows that a selective diagnosis of the conditions of the operation and status of the two closing elements 6, 8 is possible. An independent invention is established by the above diagnostic approach for dual seat valves.

BRIEF SUMMARY OF THE INVENTION

The object of the invention is achieved with the inventive diagnostic method. A measuring device for performing the diagnostic method is also described below. The use of the diagnostic method and of the measuring device to perform it for special poppet valves are also described below.

The diagnostic method to achieve the presented objective provides measuring a displacement-time curve h(t) of a displacement h of the at least one closing element at the same time as the speed-time curve of the actuating force F1(*t*) or of the reaction force F2(*t*), and the speed-time curve of the actuating force and reaction force and the displacement-time curve are combined with each other, and a force-displacement curve of the actuating force F1(*h*) or of the reaction force F2(*h*) is calculated therefrom. The current force-displacement curve of the actuating force F1(*h*) functioning as the action force, or the reaction force F2(*h*) of a switching cycle determined in this manner during the operation or life of the poppet valve is compared with an earlier one that has been saved. From the comparison according to the invention, deviations are determined that are accepted within a specified tolerance range for these deviations, or that generate a message and/or control signal when the specified tolerance range is exceeded by these deviations.

The site for recording the actuating force given the above-explained interaction of forces in the assigned adjusting rod is somewhere between the closing element and the exit of the adjusting rod out of the drive in the region of the lantern housing. If the force-time curve for the reaction force $F2(t)$ is used in the diagnostic method, then the site for recording the reaction force lies in the region surrounding the adjusting rod and between the drive and valve housing. As provided in an embodiment of the measuring device for performing the diagnostic method, this recording site advantageously lies on or in the bearing region of the lantern housing through which the flow of reaction force must be guided. The recording site for the reaction force can, however, also be located at a connecting point between the lantern housing and valve housing, or between the lantern housing and drive, wherein the connecting means itself at the connecting point can also be used as an optional site. The force is not measured directly by means of force sensors, but indirectly by measuring the expanding deformation generated by the actuating or reaction force using expansion sensors that for example are preferably embodied as so-called strain gauges.

In the comparison according to the invention, deviations are determined which are accepted within a specified tolerance range for these deviations, or which generate a message in the form of a wear, service or damage message (acoustic or visual output, printed output, etc.) and/or a control signal when the specified tolerance range is exceeded.

Determining the displacement in the above-describe manner is complex to design, and additional installation height is required in the form of the aforementioned control unit. To simplify the determination of displacement, the invention proposes determining the displacement by means of an indirectly representative physical quantity within the poppet valve, wherein expansion caused by the generated displacement in the drive at a suitable location is used as the physical quantity. For its measurement, the aforementioned expansion sensors can be used. The forces expanding the drive during the generation of its displacement result from the pretension of the spring piston drive, and these forces are adequately reflected by the spring. Once the spring characteristic is known—generally a Hooke's curve—the spring path can be calculated from the determined expansive force and hence the displacement position of the closing element.

The advantage of diagnosing with the force-displacement curve $F1(h)$ or $F2(h)$ in comparison to diagnosing with the force-time curve $F1(t)$ or $F2(t)$ is that significant events and state changes are assigned directly to the respective displacement position of the poppet valve and thus can much easier be interpreted than a time-based assignment. In addition, evaluating force-time curves while directly comparing current and earlier curves is difficult since unusual circumstances during the operation of the poppet valve which are not ascribable to state changes of the poppet valve but rather, for example, to outside influences, can lengthen or shorten the time axis of the displacement-time curve.

To determine the displacement-time curve h(t), it is known per se to determine the respective displacement h by means of direct displacement measurement. It is known in this context to record the current position of a poppet valve by means of a continuously-operating position indicator that, for example, is accommodated in a control unit arranged on the side of the drive facing away from the valve housing. The displacement position of the closing element is thereby generally indicated by the adjusting rod of the closing element which is guided through the drive into the control unit, wherein the position indicator detects the displacement position of the adjusting rod and supplies a measuring signal proportional to the displacement. A related displacement measuring system is for example described in WO 02/093 058 A1 or EP 1 387 975 B1.

For the comparison of the switching cycles to be configured as simply as possible and ensure uniform initial conditions, it is proposed that the switching cycle in a sequence over time consists of at least a closed position, an opening movement, an open or partially open position and/or at least an open or partially open position, a closing movement and a closed position.

In regard to the comparison itself, the invention proposes three preferred variants. One first variant provides an accepted switching cycle measured at the start of the poppet valve's operation or life is respectively used for the comparison. This can for example be the switching cycle of a new poppet valve, or one after a specific clearly delimited break-in phase. The second variant proposes always comparing the measured, current switching cycle with the last measured and accepted one. In addition, the tolerance range according to the invention can be adequately shifted with the last measured and accepted switching cycle. In this manner, changes in the poppet valve (such as settling or temperature-related deformations) that do not originate from state changes of the poppet valve to be diagnosed can be compensated and do not generate an error or maintenance message, or an undesired control signal.

The third variant of the method enhances the database of compared quantities by comparing the measured, current switching cycle with the average of a predetermined number of most recently measured and accepted switching cycles. This average can be the so-called arithmetic average or the geometric average. It is also advantageous to use the so-called "floating" average in which the last measured switching cycle is incorporated in the respective averaging, and the oldest switching cycle is discarded. This type of averaging has the same effect as shifting the tolerance range associated with the above-described second variant of the method.

The invention also proposes using the slope or curvature or the value of the curves at respectively predetermined discrete points of comparison, and/or at least the changes in value or surface integral of the curves at predetermined, discrete time or path intervals $\Delta t$, $\Delta h$ when comparing the force-time curves of the actuation force $F1(t)$, or of the reaction force $F2(t)$, or the force-displacement curves of the actuating force $F1(h)$ or of the reaction force $F2(h)$ in the context of the above described diagnostic method. The surface integral under the force-displacement curve $F1(h)$, $F2(h)$ at a predetermined displacement interval $\Delta h$ is particularly useful; i.e., when the seat seal is entering the assigned seat surface; this is the compression work:

$$W12 = \int_{h1}^{h2} F(h)dh$$

along the path of deformation $\Delta h = h1 - h2$, and it is the decompression work $W21$ at the seat seal along the path of deformation $\Delta h = h2 - h1$ when exiting therefrom. An intact seat seal generates different compression or decompression work than a partially, half or completely pulled out seat seal.

The diagnostic method according to the invention is suitable for identifying a poppet valve design that is to be used. This is done by using the force-displacement curve of the actuating force or of the reaction force F1(h, F2(h) at the beginning of the operation or life of the poppet valve to identify the design of the poppet valve, and the poppet valve specified in this manner is then subject to a preliminary adjustment with setting and/or monitoring data. As the measuring curves which are shown and explained below reveal, each poppet valve design possesses a significant, reproducible, unique force-time curve, or force-displacement curve, during a switching cycle which is suitable for typification.

To execute the diagnostic method, the invention proposes a measuring device that is arranged on a poppet valve wherein the poppet valve has at least one closing element in a valve housing, wherein the valve housing is firmly connected to a drive via a lantern housing, wherein the drive is designed as a spring-piston drive supplied with pressurization medium, wherein at least one adjusting rod actuatable by the drive is provided for least one closing element and wherein an evaluation device assigned to the measuring device is arranged on the poppet valve. It has proven to be useful and in particular very practical to measure a reaction force generated by the actuating force in the lantern housing. According to the invention, it is proposed that the measuring device consists of at least one first measuring device formed by at least one expansion sensor, is arranged on the lantern housing, and is connected to an evaluation unit. The reaction force can be clearly discernible and is very easy to access for measuring in a geometrically very simple housing.

Furthermore, to indirectly measure the displacement-time curve h(t), a displacement measuring device is provided which is arranged on or in a housing jacket of the drive and which is formed by at least one additional expansion sensor and is connected to the evaluation unit, wherein a drive expansion force exists in the housing jacket that is generated as a reaction force from a pretension of a spring that resets the drive piston of the drive, and wherein the displacement measuring device is arranged on the housing jacket and is designed to measure the drive expansion force.

By means of the known spring characteristic of the spring, a clearer relationship can be established between the measured drive expansion force, the expanding force per se, and the spring path, and the displacement position of the closing element can be correspondingly determined. The displacement measuring device with the above-proposed features establishes an independent invention.

Since the lantern housing is generally designed in the form of a first lantern crossmember and a second lantern crossmember opposite it, and the reaction force to be measured is not evenly distributed to both lantern crossmembers under the given conditions of manufacturing and operation, the quality of the measuring of the reaction force is significantly improved when a measuring device according to the invention is arranged in both lantern crossmembers. The invention accordingly proposes that the lantern housing has a first lantern crossmember and a second lantern crossmember opposite it, that the first measuring device is arranged on the first lantern crossmember, and that a second measuring device is provided that is formed by at least one additional expansion sensor, is arranged on the second lantern crossmember, and is connected to the evaluation unit. In principle, the lantern housing can also have more than two lanterns crossmembers which are then each equipped in the same manner with at least one expansion sensor.

The invention further proposes arranging a first and second expansion sensor in the first measuring device, a third and fourth expansion sensor in the second measuring device, a fifth and sixth expansion sensor in the displacement measuring device, and one expansion sensor of each pair of expansion sensors is arranged in the direction of displacement, and the other is arranged in an orthogonal direction thereto. The orthogonal arrangement of the expansion sensors enables temperature compensation in a very easy manner known per se, wherein the measuring signals of the expansion sensors are evaluated in a manner that is also known per se in a so-called bridge circuit of various embodiments. The evaluation unit can be arranged in the form of an internal evaluation unit in the control unit of the poppet valve, or also in an external evaluation unit outside of the poppet valve.

The expansion sensors in the preferred embodiment as a strain gauge can be affixed to the lantern housing in a frictional connection. The time and hence displacement-dependent stress in the lantern cross-section, and hence the equally time and displacement-dependent reaction force, and hence the actuating force in the adjusting rod, can be deduced from the change in length of these strain gauges since the force-transmitting cross-section and the material of the lantern housing are known. It is generally unnecessary to know the level of the reaction force or actuating force since the expansion values which are output as stress values and are linearly proportional to the forces are sufficient in the comparative assessment of the measuring results according to the invention. The displacement measuring device can determine the respective displacement when a strain gauge is used and the spring characteristic is known.

The proposed diagnostic method for poppet valves, and the measuring device for performing the method, in the respective embodiments of the dependent claims are used for a shutoff valve with a single closing element according to claim 11, or for a double seat valve according to claim 12, or for a seat-cleaning double seat valve according to claim 13, or for a double seal valve according to claim 14.

Whereas the invention is realized in a wide range of variants of a diagnostic method for poppet valves, examples of two poppet valves are portrayed in the figures of the drawing with fundamentally different closing element configurations, that is, a shut off valve having a single closing element, and a double seat valve having two independently actuatable closing elements, wherein two different closing element and seal configurations are portrayed for the double seat valve, and the calculable force-time curves F2=f(t) and force-displacement curves F2=f(h) of a reaction time F2 are portrayed along with their job-dependent meaning relative to the state of the respective poppet valve. Furthermore, two advantageous embodiments of a measuring device are portrayed that can measure a reaction force F2 generated by the actuating force F1 of the valve piston by means of expansion sensors. A displacement-time curve h=f(t) can be assigned to the force-time curve F2=f(t) of the reaction time F2 in conjunction with an additionally portrayed displacement measuring device that also contains expansion sensors and functions as an indirect position transducer. The portrayed method variants and embodiments described below are only examples of the invention; however, the invention is not restricted to these specially depicted examples.

BRIEF DESCRIPTION OF THE SEVERAL VIEWS OF THE DRAWINGS

In the drawings

FIG. 1a shows a meridian view of a drive having a measuring device with expansion sensors for indirectly determining the displacement according to FIG. 1, wherein the acting forces are depicted;

FIG. 1b shows a spring diagram assigned to the drive according to FIG. 1a that illustrates the relationship between the drive expansion force FA measured by the expansion sensors on the housing jacket of the drive and the current displacement h(FA), wherein the displacement h is plotted on the y-axis, and the drive expansion force FA is plotted on the x-axis;

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

Figure 1:
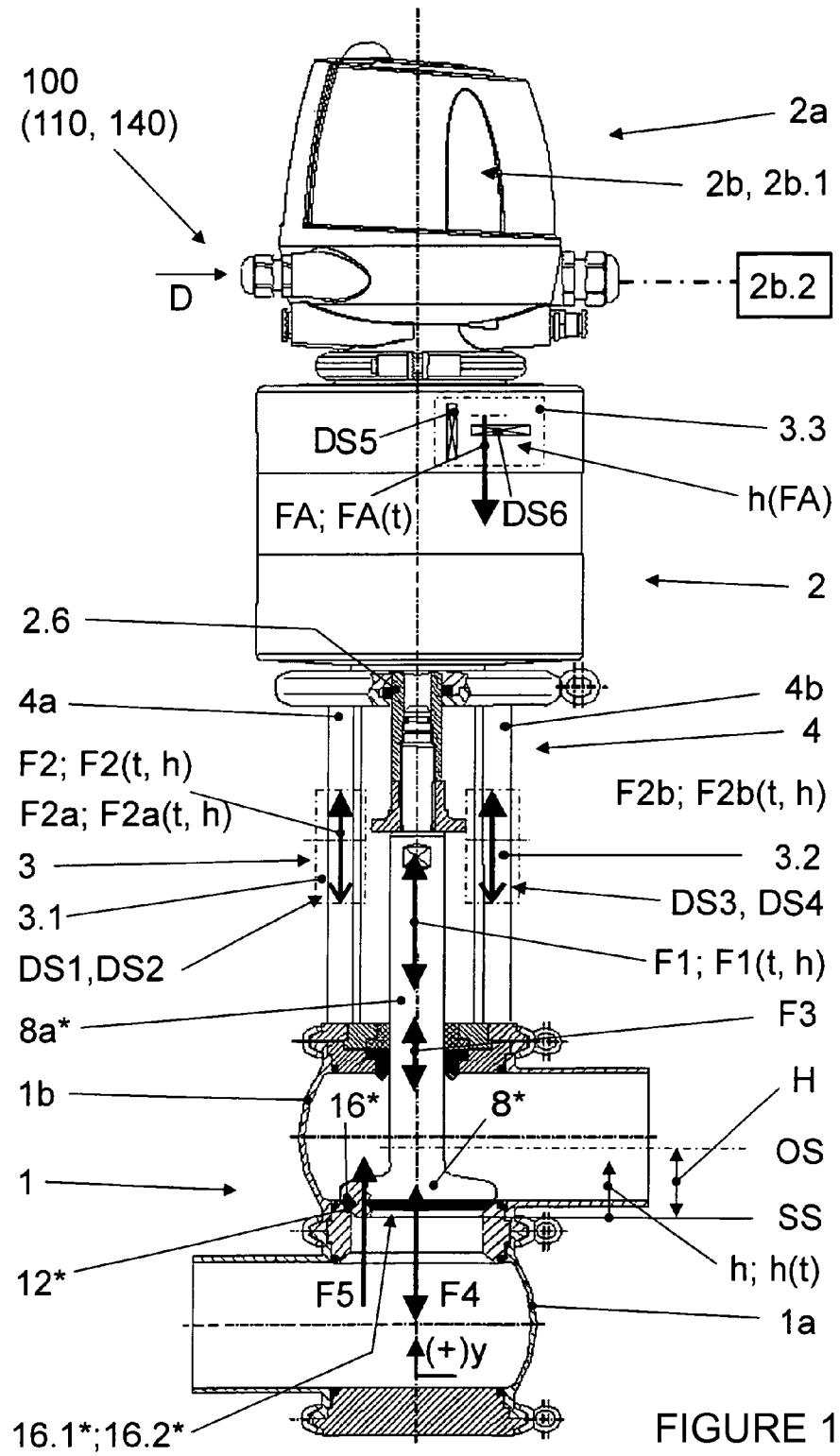
FIG. 1 shows a meridian section in the bottom part, and an exterior view in the top part, of a poppet valve designed as a shutoff valve with a single closing element, wherein two measuring devices according to the invention with expansion sensors for determining a reaction force F2 generated by the actuating force F1 of the valve rod in the lantern housing and a measuring device having expansion sensors for indirectly determining the displacement are arranged in the spring-closing poppet valve, with an indication of the individual forces (F3, F4, F5) that act on the valve rod which this actuating force F1 must overcome.
Figure 2:
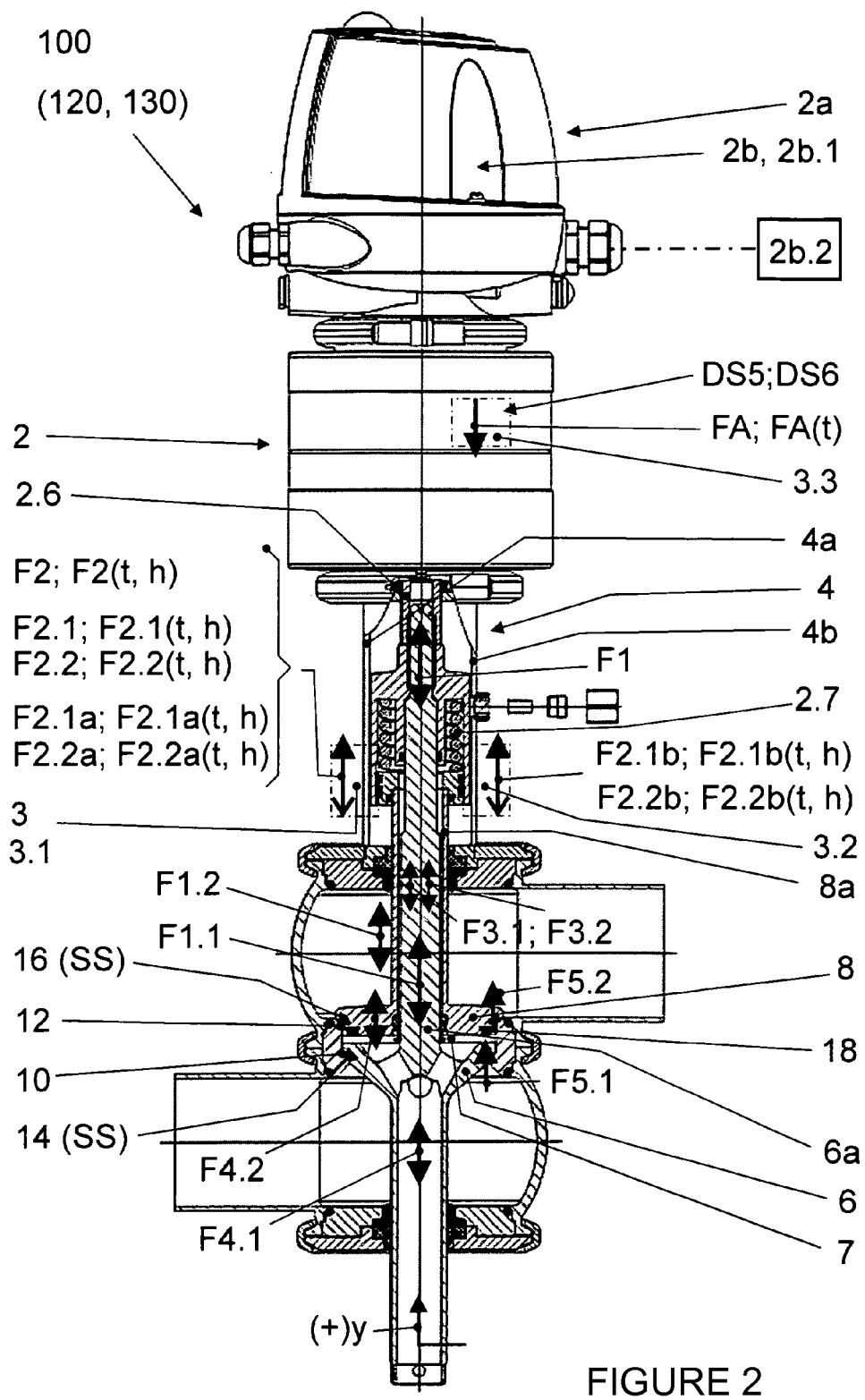
FIG. 2 shows a meridian section in the bottom part, and an exterior view in the top part, of a pocket valve designed as a double seat valve of the first kind with two independently actuatable closing elements (seat discs), wherein two measuring devices according to the invention with expansion sensors for determining a reaction force F2 generated by the actuating force F1 of the valve rod in the lantern housing and a measuring device having expansion sensors for indirectly determining the displacement are arranged on the spring-closing poppet valve, with an indication of the individual forces (F3, F4, F5.1, F5.2) that act on the valve rod which this actuating force F1 must overcome.

In the above, it has been sufficiently noted that information on the operating status of the poppet valve 100 and its general status (the status for example of the seat seal, status of the rod leadthrough, material of the seat seal, etc.) can be gleaned from the interaction of forces in the lantern housing 4 depicted in FIGS. 1 and 2. The description of FIGS. 1 and 2 will be rounded out in the following by an additional summary of the respective design of the depicted shutoff valve 110 (FIG. 1) and a double seal valve 140 (not shown) and the double seat valve 120, 130 (FIG. 2), each time in conjunction with measuring devices according to the invention.

Shutoff Valve (FIG. 1)

The poppet valve 100 designed as a shutoff valve 110 substantially consists of the valve housing 1 with the first and second valve housing part 1a, 1b, the translationally movable closing element 8* which can be designed as a seat disc as shown or as a valve piston and, in the closed position SS of the shutoff valve 110, prevents the overflow of fluid from one valve housing part 1a, 1b into the other 1b, 1a through a connecting opening connecting the valve housing parts 1a, 1b to each other (note: not all of the cited components are identified in FIG. 1, 2). The seat seal 16* of the closing element 8* interacts with the seat surface 12* directly or indirectly formed in the second valve housing part 1b, wherein the seat surface 12* in the exemplary embodiment is arranged on a seat ring that forms a connecting opening radially to the inside. The first valve housing part 1a is sealed by a housing cover by means of a so-called clamping ring on its side opposite the seat ring.

The adjusting rod 8a* is fastened to the closing rod 8* which runs sealed out of the second valve housing part 1b through a rod seal arranged at that location. It then penetrates the lantern housing 4 which is firmly connected to the drive 2, preferably by being keyed and friction locked at its end facing away from the second valve housing part 1b, for example by means of a clamping ring, and it ends in the region of the drive-side end of the lantern housing 4. In the region of the axial extension of lantern housing 4, the adjusting rod 8a* is securely connected to the piston rod 2.6 (FIG. 1a), wherein the latter penetrates a second housing face 2.3 of the drive 2 in a sealed manner, and its other end is securely connected to a drive piston 2.4 which it engages. The secure connection between the lantern housing 4 and the second valve housing part 1b is created, for example, by another clamping ring. The lantern housing 4 consists of two opposing lantern crossmembers 4a and 4b.

The drive 2 is bordered by a housing jacket 2.1 radially to the outside, and by the second housing face 2.3 to the lantern housing side, and its other end face neighbors a first housing face 2.2. The drive piston 2.4 can be moved axially and is guided radially sealed in the housing jacket 2.1, and between itself and the second housing face 2.3, it forms a pressurizing medium chamber that can be supplied with a pressurizing medium D, preferably compressed air. The spring 2.5 with the pretension FV is arranged between the drive piston 2.4 and the first housing face 2.2. The force of pressurized medium F6 exerted by the pressurized medium D on the drive piston 2.4 causes it to shift by displacement h (FIG. 1b) proceeding from the minimum pretension FVo also forming in the housing jacket 2.1 until it comes to rest on the housing jacket 2.1 after completing a full opening displacement H. During the displacement movement h between the closed position SS when h=0 and the full open position OS when h=H, an additional restoring force is generated in the spring 2.5 in addition to the minimum pretension FVo, and this is manifested as a drive expansion force FA on the housing jacket 2.1 in the form of a tensile force. This drive expansion force FA, and hence its curve over time FA(t), are measured by a displacement measuring device 3.3 that is preferably friction locked with the housing jacket 2.1. In the displacement measuring device 3.3, there is a fifth and sixth expansion sensor DS5, DS6 that are arranged there orthogonally relative to each other. The spring characteristic of the spring 2.5 (FIG. 1b) reveals a close relationship between the measured drive expansion force FA and the associated displacement h(FA), and hence the displacement position of the closing element 8*.

A control unit 2a is arranged on the first housing face 2.2 that can be supplied with pressurizing medium D to be applied to the drive 2. The pressurizing medium D can also be directly supplied in the drive 2. An evaluation unit 2b for expansion sensors DS1 to DS6 arranged on the shutoff valve can be arranged as an internal evaluation unit 2b.1 in the control unit 2a or as an external evaluation unit 2b.2 in area surrounding the shutoff valve 110.

The opening movement of the shutoff valve 110 is initiated from the portrayed closed position SS (FIG. 1, 1a), and the full open position OS is reached after the full opening displacement H is complete when the pressurizing medium D is supplied to the pressurizing medium chamber in the drive 2 along a path (not shown or identified). During the opening and closing movement of the closing element 8*, the actuating force F1 functioning as an action force is generated by the drive 2 in the adjusting rod 8*, and it must overcome the above-cited and explained forces: friction force F3, the flow and/or pressure forces F4 and the reaction force of the seat seal F5. This actuation force F1 is reflected in the lantern housing 4 as a reaction force F2, wherein this reaction force F2 is divided into a first reaction force component F2a in the first lantern crossmember 4a, and a second reaction force component F2 in the second lantern crossmember 4b in the embodiment of the lantern housing 4 with two lantern crossmembers 4a, 4b according to FIG. 1. In principle, a measuring device 3 with two expansion sensors DS1, DS2 is assigned to the lantern housing 4, and their measuring signals are processed in the evaluation unit 2b. In the exemplary embodiment in FIG. 1, a first measuring device 3.1 is preferably arranged on the first lantern crossmember 4a in a friction lock, and the first measuring device 3.1 has the first and second expansion sensors DS1, DS2 that are connected to the evaluation unit 2b in the form of the internal evaluation unit 2b.1 or the external evaluation unit 2b.2. Furthermore, a second measuring device 3.2 is arranged on the second lantern crossmember 4b in the exemplary embodiment, wherein the second measuring device 3.2 accommodates a third and a fourth expansion sensor DS3, DS4 that are connected to the evaluation unit 2b, namely in the form of the internal evaluation unit 2b.1 or the external evaluation unit 2b.2. The continuously measured reaction forces F2 yield a time and displacement-dependent curve of this reaction force F2(t), F2(h), F2a(t), F2a(h), F2b(t) and F2b(h) and hence the corresponding curve of the actuating force F1(t) and F1(h).

Double Seal Valve 140

With the double seal valve 140, the single closing element 8* possesses a first seat seal 16.1* and, at an axial distance from the latter, a second seat seal 16.2*. Both seat seals 16.1*, 16.2* can be assigned a common seat surface 12*, such as a cylindrical one which they both radially seal. The seat services can also be different and have a radial, axial or conical orientation. In regard to the interplay of forces, it should be noted that apart from the sealing force F5, the relationship of forces for the shutoff valve 110 portrayed in FIG. 1 can be applied without restriction to the double seal valve 140. Instead of sealing force F5, an assigned sealing force arises from each of the two seat seals 16.1* and 16.2* that can be detected separately providing that they engage with the common seat surface 12* at different times. From the above, it can be seen that the diagnostic method according to the invention and the measuring device to perform it can be applied without restriction to the double seal valve 140.

Double Seat Valve 120, 130 (FIG. 2)

The differences between the double seat valve 120, 130 (FIG. 2) and the shutoff valve 110 (FIG. 1) in terms of the closing element and seat configuration have already been noted above as well as the relationship of forces to describe the actuation force F1 on the piston rod 2.6 by the equations (3) to (5) (F1=F1.1+F1.2) and the resulting reaction force F2 in the lantern housing 4 according to equation (6) (F1=F2).

In regard to the additional nomenclature, it should be noted that also the reaction force F2 can be differentiated with regard to the two closing elements 6, 8. The reaction force F2 comprises a first reaction force F2.1 arising from a first closing element 6 and a second reaction force F2.2 arising from a second closing element 8 which can be detected by the measuring device 3 arranged on the lantern housing 4. Corresponding time and displacement-dependent reaction force curves are identified as F2.1(t), F2.1(h), F2.2(t) and F2.2(h). In a preferred embodiment, the lantern housing 4 consists of the above-described two lantern crossmembers 4a, 4b so that the first and second measuring device 3.1, 3.2 arranged there can measure a first reaction force component F2.1a from the first closing element 6 and a first reaction force component F2.2a from the second closing element 8 on the first lantern crossmember 4a, and can measure a second reaction force component F2.1b from the first closing element 6 and a second reaction force component F2.2b from the second closing element 8 on the second lantern crossmember 4b. Corresponding time and displacement-dependent reaction force curves are identified as F2.1a(t), F2.1a(h), F2.2a(t), F2.2a(h), F2.1b(t), F2.1b(h), F2.2b(t) and F2.2b(h).

In the control unit 2a (FIG. 1, 2) for these poppet valves 100 that are preferably arranged on the side of the drive 2 facing away from the poppet valve 100, there can be a processor to which the expansion sensors DS1 to DS6, for example in the form of strain gauges for monitoring valve operation, can be connected. The control unit 2a can also have a device for detecting and saving operating variables and characteristics of the poppet valve 100, and a device for detecting and saving the digitized measuring signals of the expansion sensors DS1 to DS6. It can also accommodate a known displacement measuring device for directly measuring displacement.

Diagrams (FIG. 3 to 7)

Figure 3:
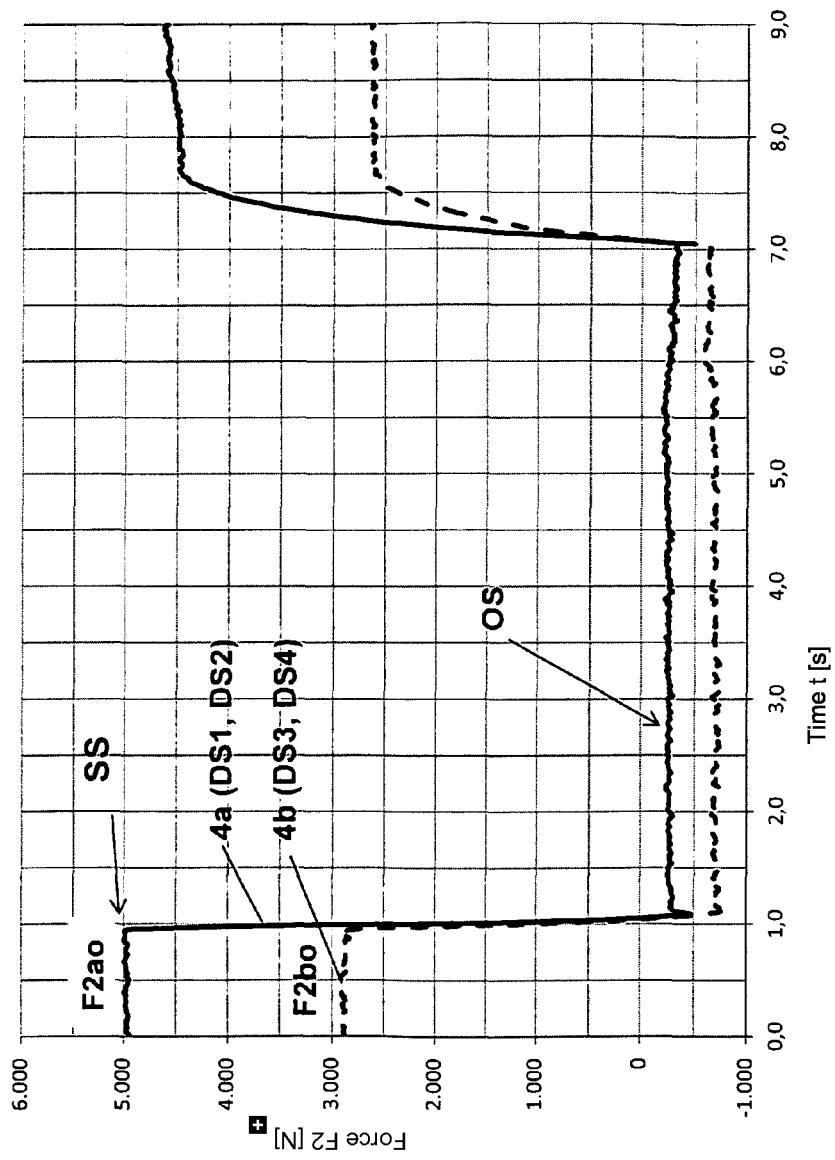
FIG. 3 shows a diagram of the respective force-time curve F2=f(t) of the reaction force F2 in each of the two lantern crossmembers of a shutoff valve according to FIG. 1, wherein the reaction force F2 is plotted on the y-axis, and the time t is plotted on the x-axis.

In the diagram in FIG. 3, the time curve F2(t) of the reaction time F2 of a shutoff valve 110 with a new seat seal 16*(FIG. 1) measured with the first measuring device 3.1 and second measuring device 3.2 according to the invention is depicted for a switching cycle, wherein the curve identified as 4a was measured in the first lantern crossmember 4a, and the curve identified as 4b was measured in the second lantern crossmember 4b. With reference to the sequence over time and starting from the closed position SS with h=0 (left area of the measuring curves), the switching cycle begins with an opening process, the closing element 8* remains for a while in an open position OS (middle area of the measuring curves) after fully opening into open position H, and then closes back to the closed position SS.

Proceeding from a positive first reaction force component F2ao and a positive second reaction force component F2bo in the closed position SS, and at the beginning of an operating or life cycle under the influence of the tensile forces in the lantern cross members 4a, 4b, the respective reaction force component significantly falls toward the value zero when force is no longer applied to the seat seal 16* and it subsequently leaves to the seat surface 12* (FIG. 1) during the opening movement. When the seat seal 16* has completely released from its seat surface 12* and the closing element 8* has moved into the full the open position H, only negative reaction forces F2 (pressure forces) are active that, in the present case, result from the friction force F3 in the leadthrough for the adjusting rod 8a*. When the closing element 8* then enters into the closed position SS from the open position OS, the relationship between the forces accordingly reverses.

In the full open position OS with h=H, the drive piston 2.4 in the drive 2 (FIG. 1a) is subject to the pressure of the pressurizing medium D generating the pressurizing medium force F6, and it comes to rest on a stop on the housing jacket 2.1. The piston rod 2.6 and hence the adjusting rod 8a* are not subject to forces from the seat seal 16* and the rod leadthrough; at most, flow forces F4 remain, thus yielding a largely force-free state in the lantern cross members 4a, 4b (F2=0 for h=H). At the beginning of the opening phase and at the end of the closing phase (h→0) when the seat seal 16*it is still, or again, pressing against the seat surface 12*, the largest pressure F1 predominates in the adjusting rod 8a*, and hence the greatest tensile force F2 predominates in the lantern cross members 4a, 4b. When the poppet valve (h=0) is in closed position SS, the closing element 8* is pressed on its seat surface 12* by the adjusting rod 8a* under the minimum pretension FVo provided in the drive of the spring 2.5 on its seat surface 12* when pressurizing medium is not applied to the drive piston 2.4. The actuating force F1 and hence the reaction force F2 then reach their maximum amount (F1=F2; F2=F2o=F2ao+F2bo). The deviating levels of force in geometrically identical lantern cross members 4a, 4b are explained by the production tolerances and intrinsic stresses arising from manufacturing and installation. As long as the seat seal 16* under this minimum pretension FVo can escape in its sealing groove, the closing element 8* lies metallically against the seat surface 12*. During the opening and closing displacement, the spring 2.5 is pretensioned with a pretension FV=FVo+FA beyond the minimum pretension FVo (see FIG. 1a, 1b), with FA being the drive expansion force. The drive expansion force FA is not manifested as a component of the reaction force F2; its opposing forces lie within the drive 2.

The force-time curve F2=f(t) between the start of opening in the end of closing of the poppet valve 110 is significant and typical for the respective state of the poppet valve, in particular in the region of its seat seal 16* and the leadthrough for the adjusting rod 8a* in the region of the second valve housing part 1b.

To enable an easy and clear comparison of the force-time curves F2(t) of switching cycles that were measured at different times during the operation or life of the poppet valve 100, it is useful to standardize the forces and associated times of the measured force-time curves of the actuating force F1(t) or of the reaction force F2(t) to ensure comparability. The force time curve F2(t) according to FIG. 3 could be standardized using the first reaction force component F2ao and F2bo in reference to the forces F2 in the closed position and at the beginning of the operating or life cycle. The times t assigned to the standardized force levels can be standardized for example by using an opening time t1 or closing time t2 explained below with reference to FIG. 5.

Figure 4:
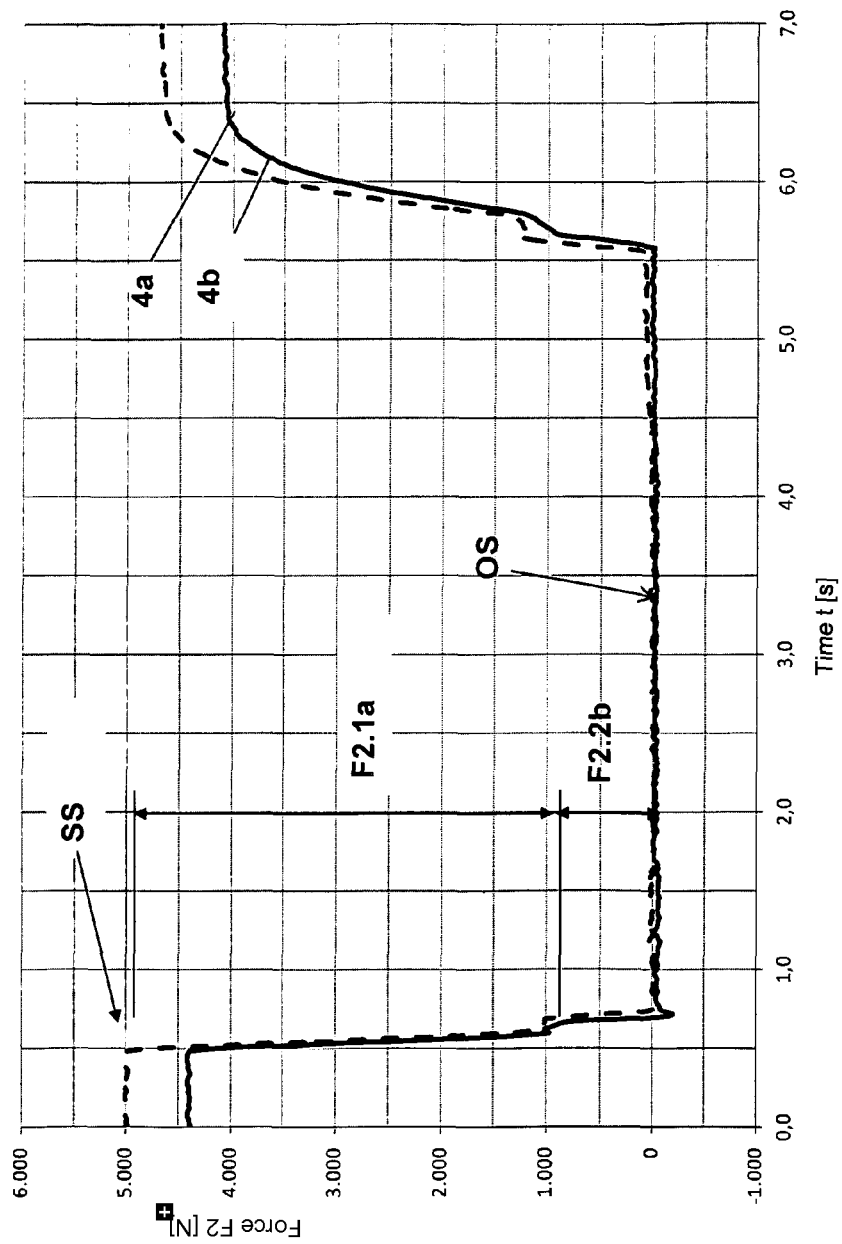
FIG. 4 shows a diagram of the respective force-time curve F2=f(t) of the reaction force F2 in each of the two lantern crossmembers of a double seat valve of the first kind according to FIG. 2, wherein the reaction force F2 is plotted on the y-axis, and the time t is plotted on the x-axis.

In the diagram in FIG. 4, the time curve F2(t) of the reaction time F2 of a double seat valve 120, 130 with two new seat seals 14, 16 (FIG. 2) measured with the first measuring device 3.1 and second measuring device 3.2 according to the invention is depicted for a switching cycle, wherein the curve identified as 4a was measured in the first lantern crossmember 4a, and the curve identified as 4b was measured in the second lantern crossmember 4b. With regard to further details of the switching cycle, reference is made to the description of FIG. 3. Over the course of their respective opening and closing process, there is a significant difference in the respective characteristic of the shutoff valve 110. It can be seen in conjunction with FIG. 2 that the first reaction force component F2.1a generated by the first closing element 6 initially decreases during the opening displacement of the first lantern crossmember 4a because its first seat seal 14 is decompressed when it leaves the assigned first seat surface 10 analogous to the seat seal 8* of the shutoff valve 110. Then as the opening movement continues and the second seat seal 16 also leaves its assigned second seat surface 12, the first reaction force component F2.2a generated by the second closing element 8 decreases. The situation is accordingly comparable for the second lantern crossmember 4b. The force-time curves F2(t) of the reaction force F2 measured with the measuring devices 3.1 and 3.2 according to the invention accordingly allow the two seat seals 14, 16 to be selectively detected and diagnosed along with the components that directly or indirectly accommodate them.

Figure 4A:
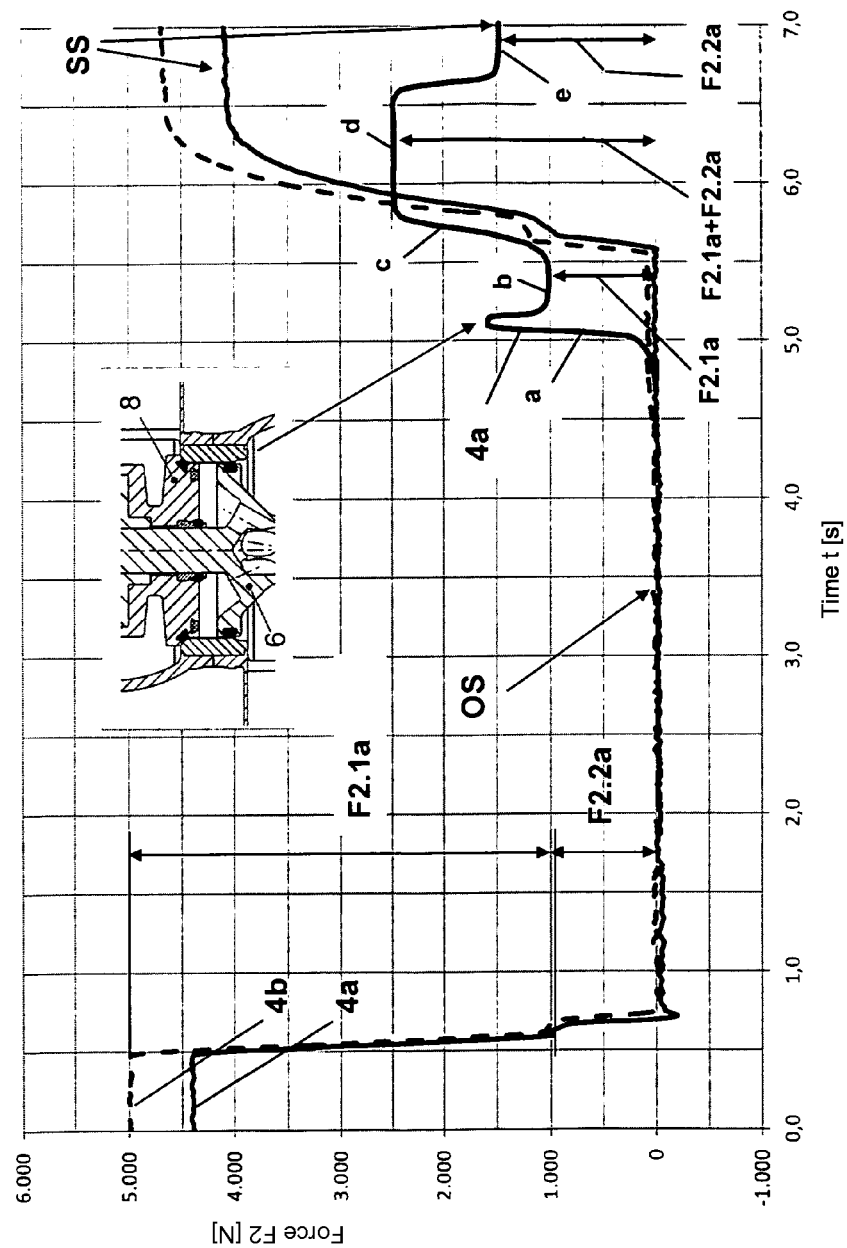
FIG. 4a shows the diagram according to FIG. 4 with an additional force-time curve F2=f(t) of the reaction force F2 when entering the closed position of a double seat valve of the second kind having a first closing element designed as a valve piston, and a second closing element designed as a seat disc.

In addition to the diagram in FIG. 4, the diagram in FIG. 4a shows a force-time curve F2(t) of the reaction force F2 when a first closing element 6 designed as a valve piston of double seat valve of the second kind is entering the closed position SS (see the small image in FIG. 4a) measured for example at the first lantern crossmember 4a. In area "a" of the curve, the first seat seal 14 of the closing element 6 rests on the edge of the cylindrical first seat surface 10. After entering the first seat surface 10, the first seat seal 14 slides into it, and during this travel, the reaction force decreases to the first reaction force component F2.1a (area "b") until the second seat seal 16 sits on the assigned second seat surface 12. This sitting and subsequent compression of the first seat seal 16 are expressed by a rise in force (area "c") by the amount of the first reaction force component F2.2a from the second closing element 8 which overlaps the first reaction force component F2.1a (area "d": F2.1a+F2.2a). Subsequently, the first closing element 6 releases from the second closing element 8 that is pressed against the assigned second seat surface 12 with the first reaction force component F2.2a (pretension F2.2a of the second spring 2.7) where it rests. When the first closing element 6 reaches its end position in the cylindrical first seat surface 10, the first reaction force component F2.1a resulting from the shifting movement disappears, and the second reaction force component F2.2a (area "e") resulting from the pretension of the second spring 2.7 remains permanently in the closed position SS.

This in turn illustrates that the force-time curves F2(t) of the reaction force F2 measured with the measuring devices 3.1 and 3.2 according to the invention for the double seat valve of the second kind as well allow the two seat seals 14, 16 to be selectively detected and diagnosed along with the components that directly or indirectly accommodate them.

Since the force curves of the above-described double seat valves of the first and second kind significantly and clearly differ from each other, the diagnostic method according to the invention makes it possible to determine the specific double seat valve design by determining the assigned force curves (automatic typification). This resulting typification can in turn be used according to the invention to perform certain necessary initial settings of the poppet valve at the beginning of its operation or life (such as the initial setting of tolerance ranges and service intervals).

Figure 5:
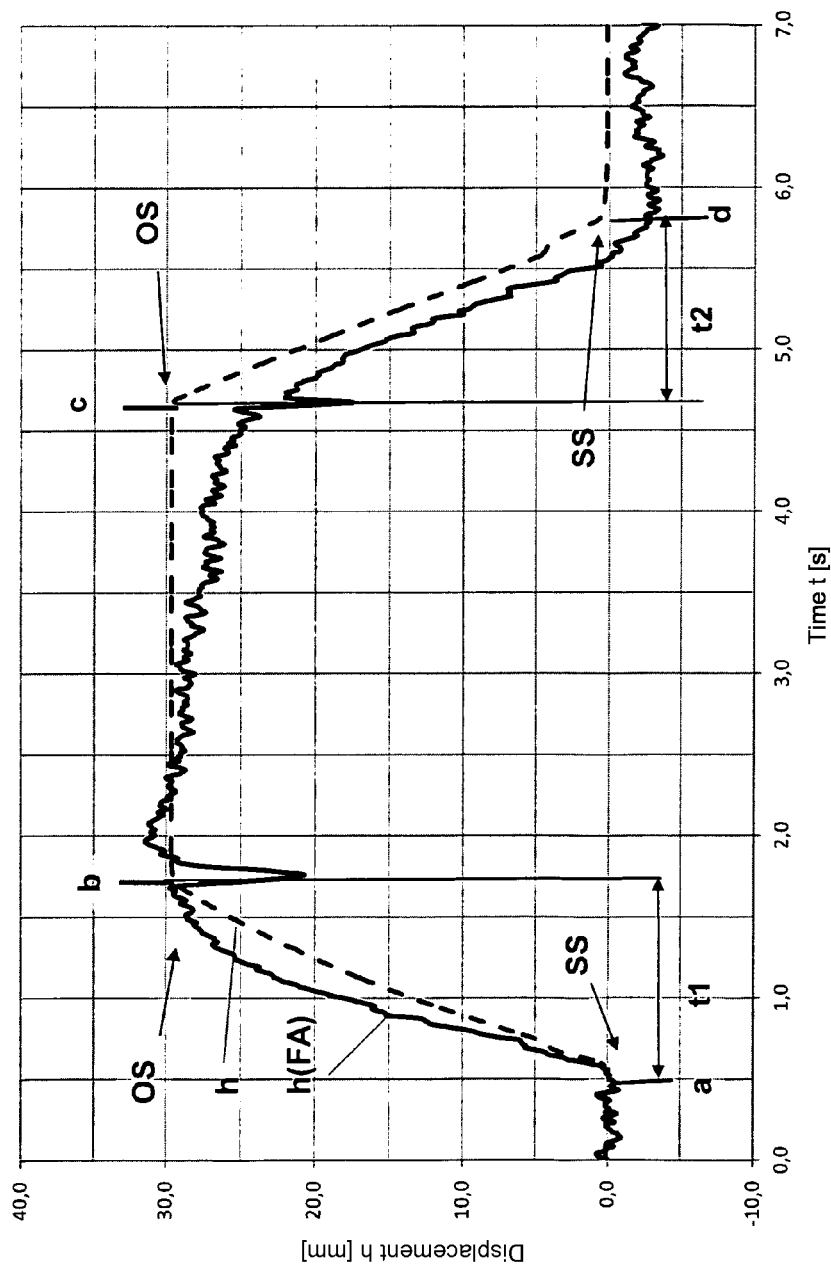
FIG. 5 shows a diagram of the indirectly determined displacement-time curve h(FA)=f(t) for a drive according to FIG. 1a, 1b in comparison with a displacement-time curve h=f(t) determined by direct displacement measurement.

With the displacement measuring device 3.3 arranged on the drive 2 according to the invention (FIG. 1a, 1b), the displacement h(FA) of the poppet valve 100 (110, 120, 130, 140) can be determined indirectly as a function of the time (h(FA)=f(t)) as shown in FIG. 5 and explained above. The displacement curve h=f(t) determined at the same time as the displacement curve h(FA)=f(t) using a familiar displacement measuring device which is preferably arranged in the control unit 2a of the poppet valve 100 (FIG. 1, 2) reveals a surprising correspondence between the two curves. The reaching of the open position OS (displacement position b) or the leaving of the open position OS (displacement position c) is respectively indicated by a significant, sudden change in the displacement curve h(FA)=f(t). This change is explained by the conditions of metallic contact between the drive piston 2.4 and housing jacket 2.1 in the drive 2. Since the closed position SS is also clearly detectable from the displacement curve h(FA)=f(t) (displacement positions a and d), the closing time t1 and the opening time t2 of the poppet valve 100 can be automatically determined for additional diagnostic steps using the displacement measuring device 3.3 according to the invention.

Figure 6:
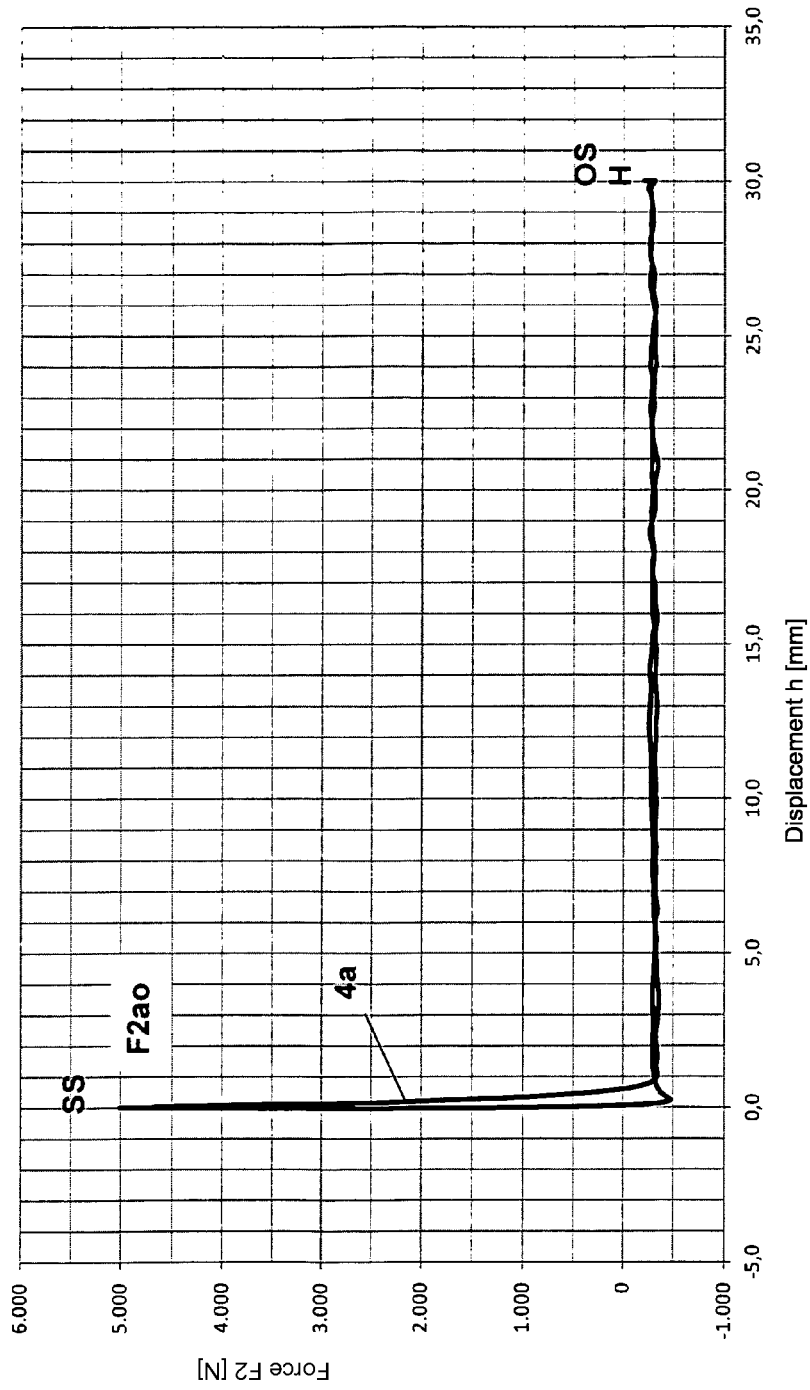
FIG. 6 shows a diagram of the force-displacement curve F2=f(h) of the reaction force F2 in a lantern crossmember of a shutoff valve according to FIG. 1 with a new and intact seat seal, wherein the reaction force F2 is plotted on the y-axis, and the displacement h is plotted on the x-axis.

The result of associating the force-time curve F2=f(t) measured at the first lantern crossmember 4a according to FIG. 3 with the directly measured displacement-time curve h=f(t), for example according to FIG. 5, wherein the curves were determined for a shutoff valve 110 with a new, intact seat seal 16*, is displayed in FIG. 6. The unbroken force-displacement curve F2=f(h) runs counterclockwise like all additional, related curves according to FIGS. 6a, 6b and 7.

Figure 6A:
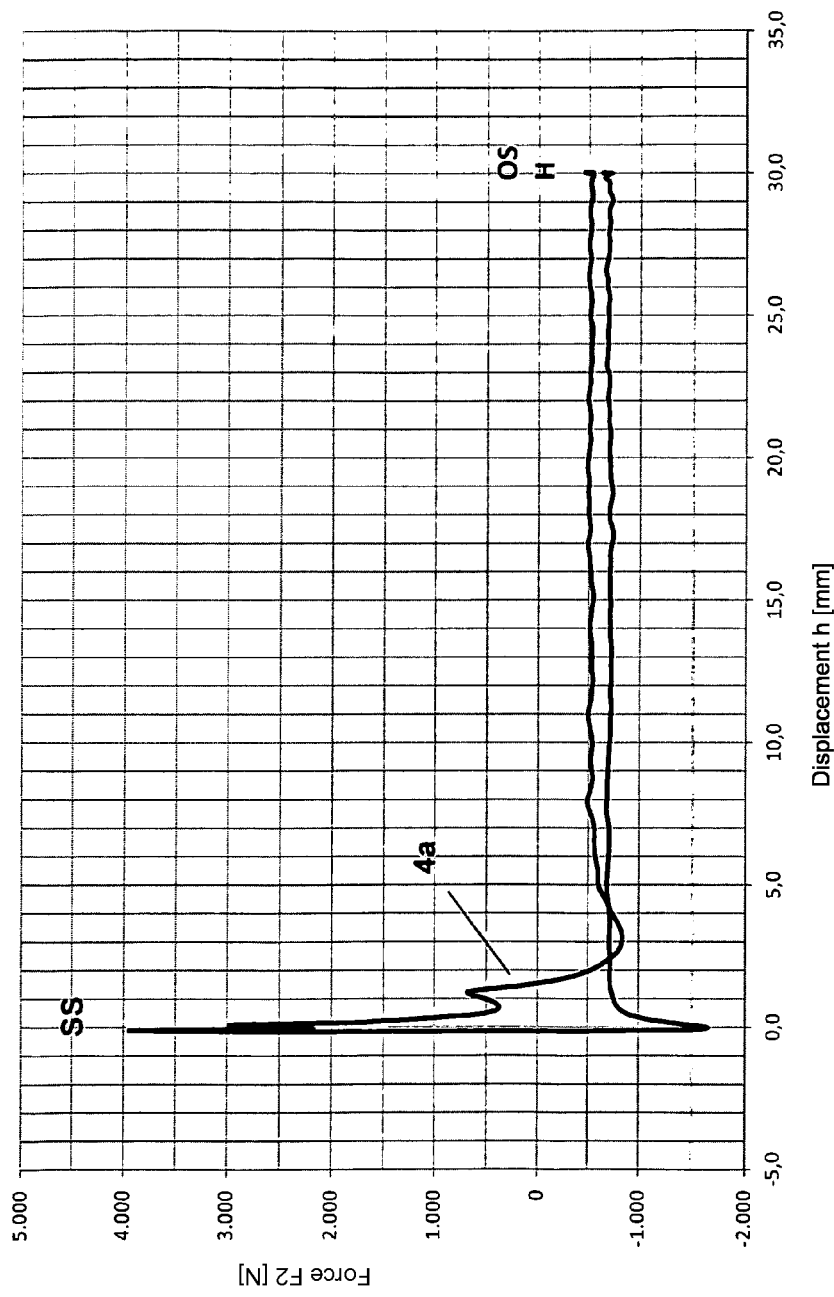
FIG. 6a shows a diagram of the force-displacement curve F2=f(h) of the reaction force F2 in a lantern crossmember of a shutoff valve according to FIG. 1 with a partially torn-out seat seal.

If this shutoff valve 110 is equipped with a partially removed seat seal 16* under the same measuring and evaluation conditions, the force-displacement curve F2=f(h) results which can be seen in FIG. 6a. A shutoff valve 110 that is switched without any seat seal 16* reveals the force-displacement curve F2(h) shown in FIG. 6b under the same measuring and evaluation conditions.

Figure 6B:
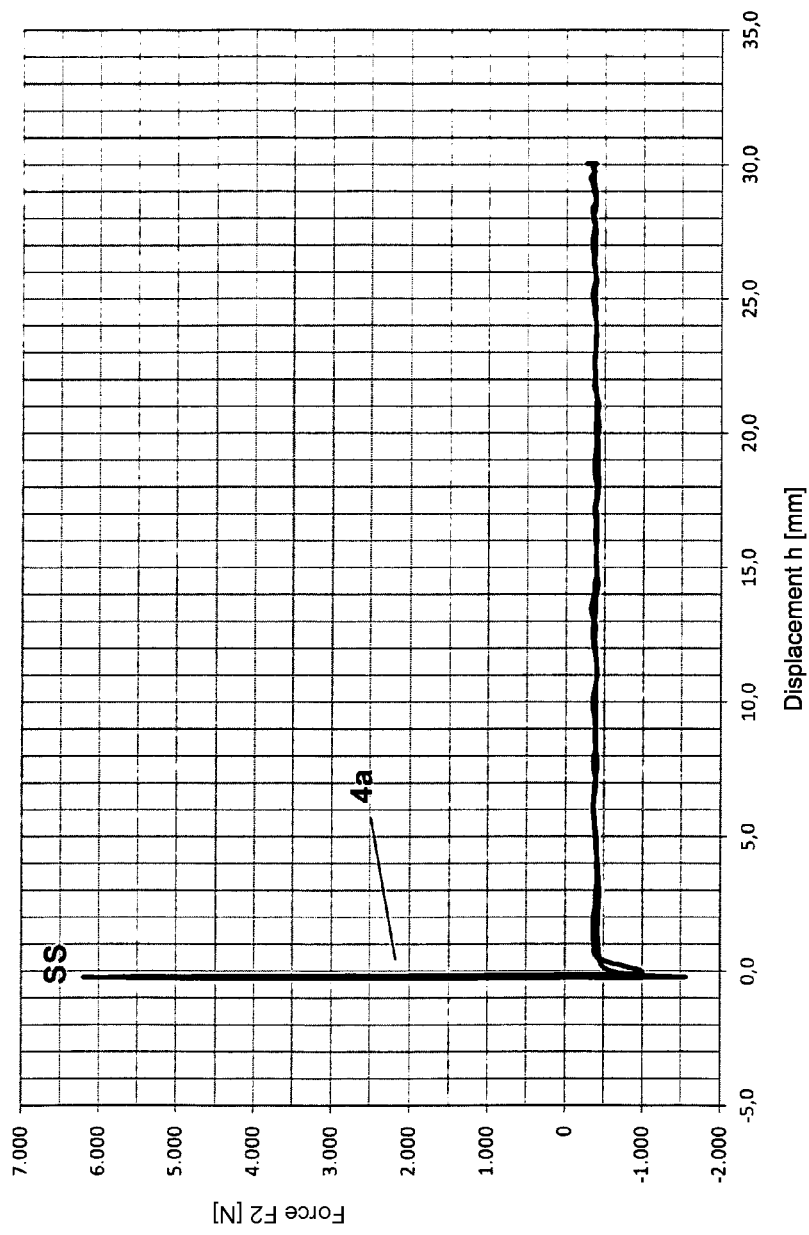
FIG. 6b shows a diagram of the force-displacement curve F2=f(h) of the reaction force F2 in a lantern crossmember of a shutoff valve according to FIG. 1 with a completely removed seat seal.
Figure 7:
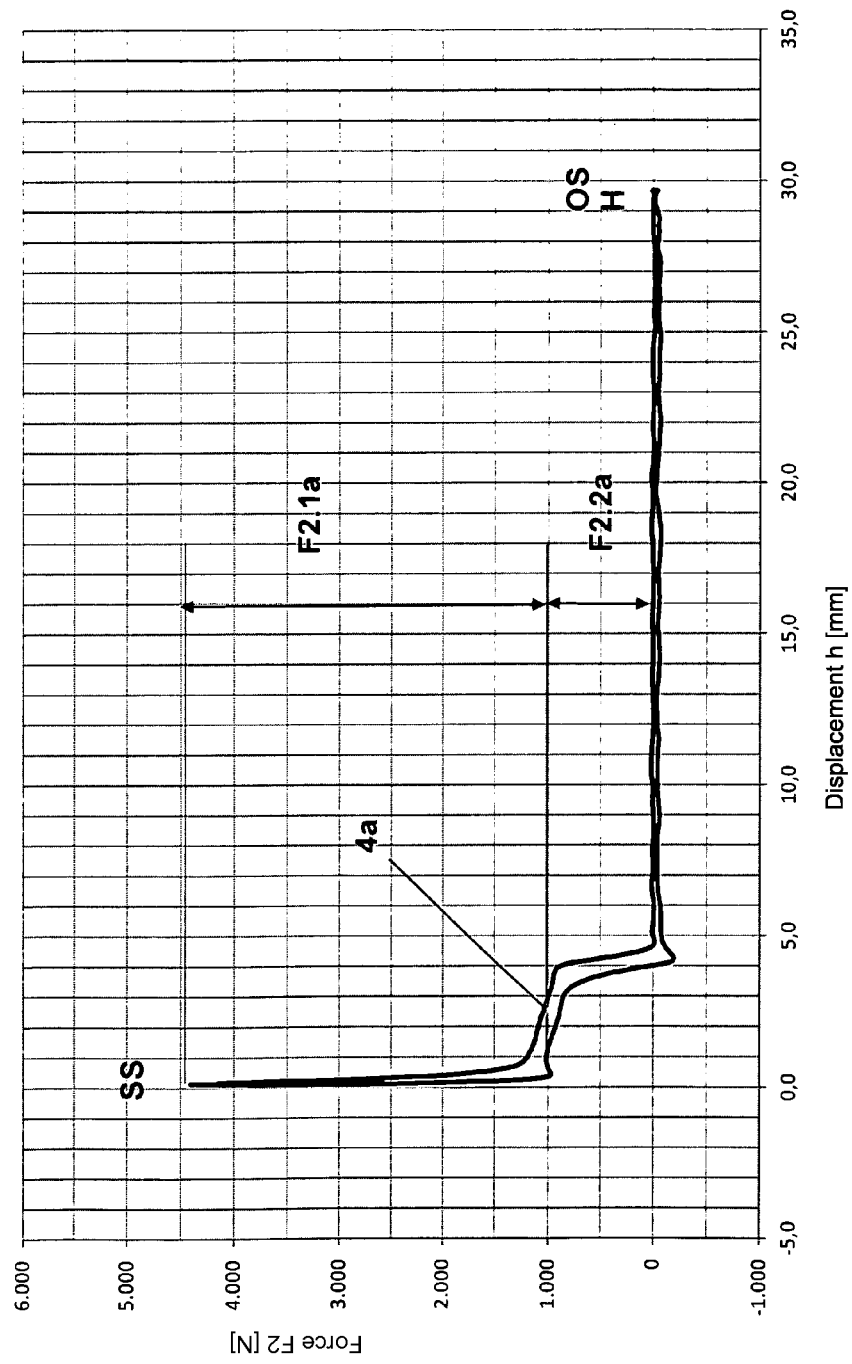
FIG. 7 shows a diagram of the force-displacement curve F2=f(h) of the reaction force F2 in a lantern crossmember of a double seat shutoff valve according to FIG. 2 with a new and intact seat seal, wherein the reaction force F2 is plotted on the y-axis, and the displacement h is plotted on the x-axis.

For a double seat valve 120, 130 according to FIG. 2 with new, intact seat seals 14, 16, the measuring devices 3.1, 3.2 according to the invention yield the force-displacement curve F2(h) shown in FIG. 7 with direct measurement of the path of displacement under the above measuring and evaluation conditions. The respective entrance of the closing elements 6, 8 with their assigned seat seals 14, 16 into the seat surfaces 10, 12, as well as the respective exiting from the seat surfaces are depicted in a surprisingly clear manner in the characteristic curve. In view of the results according to FIGS. 6a and 6b when the seat seal 14 or 16 is partially or completely removed, the state of the seat seals 14, 16, the friction ratio at leadthroughs for the adjusting rods 6a, 8a, the completion of the closed position SS and the full open position OS, and in the case of a seat cleaning double seat valve 130, the opening of the seat surfaces 12 and 14 by a gap while the seats are being cleaned, and hence the completion of the required partial displacement for it, can be detected and diagnosed with the assistance of the diagnostic method according to the invention.

The measuring curves of an intact, new and normally functioning valve with a new seat seal (normal operating status of the poppet valve 100) according to FIG. 3 to 6 and FIG. 7 more or less significantly differ from the measurement curves of a poppet valve 100 with a damaged seat seal FIG. 6a, 6b) and/or damaged rod leadthrough. The differences are significant and can be unambiguously and reproducibly detected using the comparative criteria proposed according to the invention. It can also be concluded that, in particular, wear from corrosion, cavitation, erosion or mechanical damage of the entire poppet valve 100, in particular the seat seal(s) and/or the components interacting with each other, can be identified using the measurement curves. The servicing time can, for example, also be predicted.

In addition to diagnosing the state of the poppet valve 100, pressure surges and shocks at the closing elements 8* or closing elements 6, 8 in the poppet valve 100 can be detected and recorded, which also allows the monitoring of the processing progress of a processing system in which the poppet valve 100 is used.

It is particularly useful when comparing force-displacement curves F2(h) from switching cycles to use the comparative criterion of the above-addressed surface integral representing the compression work W12 or decompression work W21 at the seat seal 8*, 6, 8. By forming the surface integral under the force-displacement curve F2(h) and specifying a deviation, damage to the poppet valve 100 can be identified since the aforementioned differences in this surface integral are significant.

LIST OF REFERENCE NUMBERS FOR THE USED ABBREVIATIONS

Shutoff (Double Seal) and Double Seat Valve
100 Conventional poppet valve
110 Poppet valve (one closing element, one seat seal)
120 Double seat valve (two independently actuatable closing elements that each have one seat seal)
130 Seat cleaning double seat valve (in comparison to 120, having a separately controllable, additional partially open position for each closing element)
140 Double seat valve (one closing element with two spaced seat seals)
1 Valve housing
1a First valve housing part
1b Second valve housing part
2 Drive (spring piston drive supplied with pressurizing medium)
2.1 Housing jacket
2.2 First housing face
2.3 Second housing face
2.4 Drive piston
2.5 Spring
2.6 Piston rod
2a Control unit
2b Conventional evaluation unit
2b.1 Internal evaluation unit
2b.2 External evaluation unit 3 Conventional measuring device (for determining the force-time and/or the displacement-time curve)
3.1 First measuring device
3.2 Second measuring device
3.3 Displacement measuring device
4 Lantern housing
4a First lantern crossmember
4b Second lantern crossmember
D Pressurizing medium
DS Conventional expansion sensor
DS1 First expansion sensor (such as a strain gauge)
DS2 Second expansion sensor (such as a strain gauge)
DS3 Third expansion sensor (such as a strain gauge)
DS4 Fourth expansion sensor (such as a strain gauge)
DS5 Fifth expansion sensor (such as a strain gauge)
DS5 Sixth expansion sensor (such as a strain gauge)
F1 Actuating force (action force)
F1(t) Actuating force F1 as a function of the time t (force-time curve of the actuating force F1)
F1(h) Actuating force F1 as a function of the displacement h (force-displacement curve of the actuating force F1)
F1o Actuating force F1 in the closed position and at the beginning of the operating or life cycle
F2 Reaction force
F2(t) Reaction force F2 as a function of the time t (force-time curve of the reaction force F2)
F2(h) Reaction force F2 as a function of the displacement h (force-displacement curve of the reaction force F2)
F2o Reaction force F2 in the closed position and at the beginning of the operating or life cycle
F2a First reaction force component
F2ao First reaction force component in the closed position and at the beginning of the operating or life cycle
F2a(t, h) First reaction force component as a function of time t or displacement h
F2b Second reaction force component
F2bo Second reaction force component in the closed position and at the beginning of the operating or life cycle
F2b(t, h) Second reaction force component as a function of time t or displacement h
F3 Friction force (in the leadthrough for the adjusting rod 8a*)
F4 Flow and/or pressure forces (on the closing element 8*)
F5 Sealing force (reaction force of the seat seal(s))
F6 Pressurization medium force
FV Spring pretension (for h>0)
FVo Minimum spring pretension (for h=0)
FA Drive expansion force (on the housing jacket 2.1) (excessive relative to FVo and for 0≤h≤H; FA=FV−FVo)
FA(t) Drive expansion force as a function of time t
H Opening displacement (full open position)
OS Open position (h=H)
SS Closed position (h=0)
W12 Compression work in displacement interval Δh=h1−h2
W21 Decompression work in displacement interval Δh=h2−h1
a, b, c, d, e Displacement positions
h Displacement (any displacement between h=0 and h=H)
h(t) Displacement h as a function of time t (displacement-time curve)
h(FA) Displacement h determined from FA
Δh Deformation path of the seat seal, displacement interval (Δh=h1−h2)
t Time
Δt Time interval
t1 Opening time
t2 Closing time
y y-axis (upward (+)y direction)
Shut Off Valve 110, (Double Seal Valve 140)
8* Closing element
8a* Adjusting rod
12* Seat surface
16* Seat seal
(16.1*) First seat seal
(16.2*) Second seat seal
Double Seat Valve 120, 130
2.7 Second spring
6 First closing element
6a First adjusting rod
7 Leakage cavity
8 Second closing element
8a Second adjusting rod (hollow rod)
10 First seat surface
12 Second seat surface
14 First seat seal
16 Second seat seal
18 Middle seal
F1.1 First actuating force (first closing element 6)
F1.2 Second actuating force (second closing element 8)
F2.1 First reaction force (first closing element 6)
F2.1(t, h) First reaction force as a function of time t or displacement h
F2.1a First reaction force component (first closing element 6)
F2.1b Second reaction force component (first closing element 6)
F2.1a(t, h) First reaction force component as a function of t, h (first closing element 6)
F2.1b(t, h) Second reaction force component as a function of t, h (first closing element 6)
F2.2 Second reaction force (second closing element 8)
F2.2(t, h) Second reaction force as a function of time t or displacement h
F2.2a First reaction force component (second closing element 8)
F2.2b Second reaction force component (second closing element 8)
F2.2a(t, h) Second reaction force component as a function of t, h (second closing element 8)
F2.2b(t, h) First reaction force component as a function of t, h (second closing element 8)
F3.1, F3.2 Friction force (in the leadthrough for the adjusting rod 6a, 8a)
F4.1, F4.2 Flow and/or pressure forces (on the closing elements 6, 8)
F5.1, F5.2 Reaction force of the seat seals 14, 16

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent claim format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A diagnostic method for poppet valves with which an actuating force (F1) representing an action force that is generated by a fluid-actuated spring piston drive (2) of the poppet valve (100) is determined for at least one closing element (8*) of the poppet valve (100) in the form of a force-time curve, the actuating force (F1) is either determined directly or from a reaction force (F2) resulting from the actuating force (F1) in the poppet valve (100), wherein the actuating force (F1) or the reaction force (F2) is determined by measuring expanding deformations caused therefrom, and the measured, current force-time curve of the actuating force (F1(t)) or of the reaction force (F2(t)) is saved and subjected to an evaluation, characterized in that
   a displacement-time curve (h(t)) of the displacement (h) of the at least one closing element (8*) is measured at the same time as the force-time curve of the actuating force or of the reaction force (F1(t); F2(t)), and the force-time curve of the actuating force or of the reaction force (F1(t); F2(t)) and the displacement-time curve (h(t)) are combined with each other, and a force-displacement curve of the actuating force or of the reaction force (F1(h); F2(h)) is determined therefrom,
   the current force-displacement curve determined during the operation or life of the poppet valve (100) of the actuating force (F1(h)) or of the reaction force (F2(h)) of a switching cycle is compared with an earlier stored force displacement curve of the actuating force F1 (h) or of the reaction force F2 (h) of an associated switching cycle,
   deviations are determined from the comparison of the actual switching cycle with the earlier switching cycle, wherein either deviation are determined to be within a predetermined tolerance range, and are accepted;
   or in the alternative, the deviations are determine to exceed the predetermined tolerance range, and a message and/or control signal is/are generated,
   the displacement (h) is determined by an indirectly representative physical quantity within the poppet valve (100), and
   expanding deformations caused by the generation of the displacement (h) in the drive (2) is used as a physical quantity.

2. The diagnostic method for poppet valves according to claim 1, characterized in that a switching cycle in a sequence over time consists of at least one closed position (SS), an opening movement, an open (OS) or partially open position, and/or at least one open (OS) or partially open position, a closing movement and a closed position (SS).

3. The diagnostic method for poppet valves according to claim 1, characterized in that an accepted switching cycle measured at the start of the operation or life of the poppet valve (100) is always used for the comparison.

4. The diagnostic method for poppet valves according to claim 1, characterized in that the measured current switching cycle is compared with the last measured and accepted one.

5. The diagnostic method for poppet valves according to claim 1, characterized in that the measured current switching cycle is compared with the average of a predetermined number of last measured and accepted switching cycles.

6. The diagnostic method for poppet valves according to claim 1, characterized in that at least one comparative criterion from those cited below is used for comparing the force-time curves of the actuating force or of the reaction force (F1(t); F2(t)), or the force-displacement curves of the actuating force or of the reaction force (F1(h); F2(h)):
   the slope
   the curvature
   the amount
   at predetermined, discrete comparative locations,
   the change in the amount
   the surface integral
   at predetermined discrete time or displacement intervals ($\Delta t$; $\Delta h$).

7. The diagnostic method for poppet valves according to claim 1, characterized in that the force-displacement curve of the actuating force or of the reaction force (F1(h, F2(h)) at the beginning of the operation or life of the poppet valve (100; 110, 120, 130, 140) is used to identify the design of the poppet valve (100), and the poppet valve (100) typified in this manner is then subject to a preliminary adjustment with setting and/or monitoring data.

8. A measuring device for performing the diagnostic method for poppet valves according to claim 1, wherein the measuring device (3) is arranged on a poppet valve (100), wherein the poppet valve (100) has at least one closing element (8*) in a valve housing (1), wherein the valve housing (1) is securely connected to a drive (2) via a lantern housing (4), wherein the drive (2) is designed as a spring-piston drive supplied with pressurization medium, wherein at least one adjusting rod (8a*) actuatable by the drive (2) is provided for least one closing element (8*), and wherein an evaluation device (2b) assigned to the measuring device (3) is arranged on the poppet valve (100), characterized in that the measuring device (3) consists of at least one first measuring device (3.1) formed by at least one expansion sensor (DS), is arranged on the lantern housing (4), and is connected to the evaluation unit (2b),
   a displacement measuring device (3.3) is arranged on or in a housing jacket (2.1) of the drive (2) which is formed by at least one additional expansion sensor (DS) and is connected to the evaluation unit (2b),
   a drive expansion force (FA) exists in the housing jacket (2.1) that is generated as a reaction force from a pretension (FV) of a spring (2.5) that resets a drive piston (2.4) of the drive (2), and the displacement measuring device (3.3) is designed to measure the drive expansion force (FA).

9. The measuring device according to claim 8, characterized in that the lantern housing (4) has a first lantern crossmember (4a) and a second lantern crossmember (4b) opposite it, that the first measuring device (3.1) is arranged on the first lantern crossmember (4a), and that a second measuring device (3.2) is provided that is formed by at least one additional expansion sensor (DS), is arranged on the second lantern crossmember (4b), and is connected to the evaluation unit (2b).

10. The measuring device according to claim 8, characterized in that a first and second expansion sensor (DS1, DS2) are arranged in the first measuring device (3.1), a third and fourth expansion sensor (DS3, DS4) are arranged in a second measuring device (3.2), a fifth and sixth expansion sensor (DS5, DS6) are arranged in the displacement measuring device (3.3), and one expansion sensor of each pair of expansion sensors (DS1, DS2; DS3, DS4; DS5, DS6) is arranged in the direction of displacement, and the other is arranged in an orthogonal direction thereto.

11. The use of the diagnostic method for poppet valves and of the measuring device for performing the method according to claim 8 for a shutoff valve (110) with a single closing element (8*).

12. The use of the diagnostic method for poppet valves and of the measuring device for performing the method according to claim 8 for a double seat valve (120) having two closing elements (6, 8) that are independently actuatable by means of the drive (2) and that enclose a leakage cavity (7) between themselves which is connected via at least one connecting path to the surrounding area of the double seat valve (120).

13. The use of the diagnostic method for poppet valves and the measuring device for performing the method according to claim 8 for a seat-cleaning double seat valve (130) having two closing elements (6, 8) that are independently actuatable by means of the drive (2) and that enclose a leakage cavity (7) between themselves which is connected via at least one connecting path to the surrounding area of the double seat valve (120), wherein the closing elements (6, 8) each have partially open positions that can be controlled separate from each other.

14. The use of the diagnostic method for poppet valves and of the measuring device for performing the method according to claim 8 for a double seat valve (140) having a single closing element (8*) with two seat seals (16.1*, 16.2*) at an axial distance from each other, that enclose a leakage cavity between themselves and in conjunction with assigned seat surfaces and the closing element (8*) that is connected via at least one connecting path to the surrounding area of the double seal valve (140).

* * * * *